United States Patent [19]

Longo et al.

[11] Patent Number: 4,865,766
[45] Date of Patent: Sep. 12, 1989

[54] PROCESS FOR THE PREPARATION OF 4-AMINO-ANDROSTENEDIONE DERIVATIVES

[75] Inventors: Antonio Longo; Fabrizio Orzi; Paolo Lombardi, all of Milan; Maristella Colombo, Cesano Boscone, all of Italy

[73] Assignee: Farmitalia Carlo Erba S.r.l., Milan, Italy

[21] Appl. No.: 192,138

[22] Filed: May 10, 1988

[30] Foreign Application Priority Data

May 15, 1987 [GB] United Kingdom ............... 8711579

[51] Int. Cl.$^4$ .............................................. C07J 1/00
[52] U.S. Cl. ................................................ 260/397.3
[58] Field of Search ..................... 514/177; 260/397.3

[56] References Cited

U.S. PATENT DOCUMENTS 4,757,061  7/1988  Faustini et al. ..................... 514/177

FOREIGN PATENT DOCUMENTS 2171100  of 0000  United Kingdom ............... 514/177

*Primary Examiner*—Douglas W. Robinson
*Assistant Examiner*—Joseph A. Lipovsky
*Attorney, Agent, or Firm*—Oblon, Spivak, McClelland, Maier & Neustadt

[57] ABSTRACT

A process for the preparation of 4-aminoandrostenediones of formula (I)

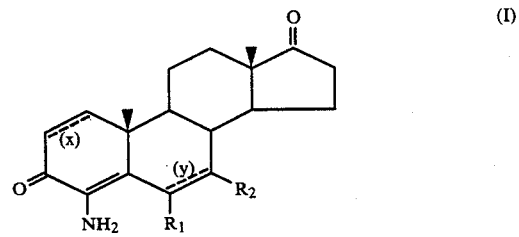

and pharmaceutically acceptable salts thereof, wherein one of $R_1$ and $R_2$ is hydrogen and the other is hydrogen, $C_1$–$C_6$ alkyl, $C_2$–$C_6$ alkenyl or $C_2$–$C_6$ alkynyl, and the symbol ==== indicates that each of (x) and (y), independently, is a single bond or a double bond, comprising reacting a compound of formula (II)

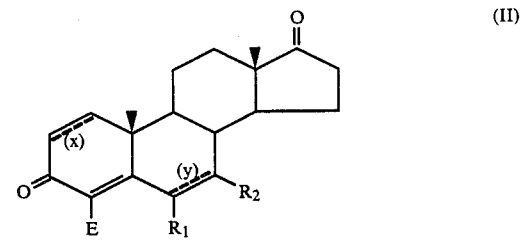

wherein E is a halogen atom and $R_1$, $R_2$, (x) and (y) each are as defined as above with ammonia.

7 Claims, No Drawings

PROCESS FOR THE PREPARATION OF 4-AMINO-ANDROSTENEDIONE DERIVATIVES

This invention relates to the preparation of 4-amino-androstenedione derivatives.

GB-A-2171100 discloses 4-substituted androstenedione derivatives. The compounds therein described can be represented by the following formula (A)

(A)

wherein
R is
(1) a group $$-N\begin{matrix}R_3\\R_4\end{matrix}$$

wherein each of $R_3$ and $R_4$ is, independently, hydrogen or unsubstituted $C_1$-$C_{22}$ alkyl;

(2) a group $-NHCOR_5$ wherein $R_5$ is
  (a) hydrogen;
  (b) $C_1$-$C_3$ alkoxy, benzyloxy or carboxy;
  (c) $C_1$-$C_{22}$ alkyl either unsubstituted or substituted by a substituent chosen from (i) halogen; (ii) carboxy; (iii) $C_4$-$C_7$ monocycloalkyl; (iv) pentatomic or hexatomic heteromonocyclic ring containing one or more heteroatoms chosen from O, N and S; and (v) unsubstituted phenyl or phenyl substituted by $C_1$-$C_6$ alkyl, $C_1$-$C_3$ alkoxy, hydroxy, halogen, tri-halo-$C_1$-$C_6$-alkyl or nitro;
  (d) $C_4$-$C_7$ monocycloalkyl;
  (e) pentatomic or hexatomic heteromonocyclic ring containing one or more heteroatoms chosen from O, S and N; or
  (f) unsubstituted phenyl or phenyl substituted by $C_1$-$C_6$ alkyl, $C_1$-$C_3$ alkoxy, hydroxy, halogen, tri-halo-$C_1$-$C_6$-alkyl or nitro;

(3) a group $-NHSO_2R_6$ wherein $R_6$ has one of the meanings reported above for $R_5$ except hydrogen; or (4) the group $-N_3$; one of $R_1$ and $R_2$ is hydrogen and the other is hydrogen, $C_1$-$C_6$ alkyl, $C_2$-$C_6$ alkenyl or $C_2$-$C_6$ alkynyl; and the symbol ==== indicates that each of (x) and (y), independently, is a single bond or a double bond; provided that R is not the group $-N_3$ when (x) is a single bond and (y) is a double bond; and the pharmaceutically acceptable salts thereof.

The compounds of formula (A) are inhibitors of the bio-transformation of androgens into estrogens, i.e., they are steroidal aromatase inhibitors. The aromatase inhibitors activity of these compounds was demonstrated by employing the in vitro test described by Thompson and Siiteri (E. A. Thompson and P. K. Siiteri, J. Biol. Chem. 249, 5364, 1974) which utilizes the human placental microsomal fraction as enzyme source. In this test the aromatization rate of androstenedione into estrone was evaluated by incubating [$1\beta,2\beta$-$^3$H]androstenedione (50 nM) in the presence of NADPH with the enzyme preparation and by measuring the amount of $^3H_2O$ formed during 20 min incubation at 37° C. The compounds, incubating at various concentrations, showed a relevant aromatase inhibitory activity.

Amid the compounds disclosed by U.K. patent application No. 2171100 A, in particular, the following ones have been found to have very interesting and valuable biological properties:
  4-aminoandrost-4-ene-3,17-dione,
  4-aminoandrosta-4,6-diene-3,17-dione,
  4-aminoandrosta-1,4-diene-3,17-dione, and
  4-aminoandrosta-1,4,6-triene-3,17-dione.

By virtue of their ability to inhibit aromatase and, consequently, to reduce estrogen levels, the compounds of formula (A) are useful in the treatment and prevention of various estrogen dependent diseases, i.e., breast, endometrial, ovarian and pancreatic cancers, gynecomastia, benign breast disease, endometriosis, polycystic ovarian diseased and precocious puberty. Another application of these compounds is in the therapeutic and/or prophylactic treatment of prostatic hyperplasia, a disease of the estrogen dependent stromal tissue.

These compounds can find also for the treatment of male infertility associated with oligospermia and for female fertility control, by virtue of their ability to inhibit ovulation and egg nidation.

According to U.K. patent application No. 2171100 A, 4-amino derivatives, namely compounds of formula (A) wherein R is a group $-NR_3R_4$, in which $R_3$ and $R_4$ are hydrogen, and $R_1$, $R_2$, (x) and (y) are as defined above are prepared by various processes all based on the reaction of a suitable androsta-3,17-dione derivative with a compound of formula (B)

$$M-N_3 \tag{B}$$

wherein M is an alkali metal or ammonium cation, or a tri$C_1$-$C_6$ alkylsilyl group, so obtaining, according to the reaction conditions, either a compound of formula (A) wherein R is a group $-NH_2$, or a compound of formula (A) wherein R is a group $-N_3$ which is then either reduced to obtain the corresponding compound in which R is $-NH_2$ or subjected to pyrolysis to obtain another compound of formula (A) in which R is $-NH_2$.

U.K. patent application No. 2171100 A provides all the details of the reactions concerned. However preferred compounds of formula (B) are sodium azide, lithium azide, ammonium azide, trimethylsilylazide and dimethyltert.butylsilylazide. The reaction between a suitable androsta-3,17-dione derivative and a compound of formula (B) is preferably carried out in an organic solvent such as, for instance, N,N-dimethylformamide, N,N-dimethylacetamide or dimethylsulfoxide; some water or an aqueous alcoholic, e.g. methanolic or ethanolic, solution may be added, if desired, to increase the solubility of the azide of formula (B). If necessary also a concentrated mineral acid, preferably concentrated sulphuric acid, may be added.

If the reaction is performed under mild conditions, such as, for instance, at low temperature, e.g. from about 0° C. to about 60° C., and for short reaction times, e.g. from some minutes to about 1 hour, a compound of formula (A) wherein R is the group $-N_3$ is obtained.

If, on the contrary, the reaction is performed under more drastic conditions, for instance at higher temperature, e.g. from about 60° C. to about 150° C., and for longer reaction times, e.g. from 30 minutes to several hours, then a compound of formula (A) is obtained wherein R is a group —NH$_2$. The reduction of a compound of formula (A) wherein R is the group —N$_3$ to give a compound of formula (A) wherein R is a group —NH$_2$, may be carried out following known methods, for example with a variety of reducing agents, e.g. propane-1,3-dithiol in triethylamine, dithiolthreitol in aqueous solutions, mercaptoacetic acid and triethylamine, or, for instance, catalyst reductions using, e.g., palladium catalysts.

The pyrolysis of a compound of formula (A) wherein R is the group —N$_3$, to give another compound of formula (A) wherein R is a group —NH$_2$, may be, e.g., carried out by heating at a temperature of 100°-150° C., for some minutes to several hours, in a suitable medium such as, for instance, N,N-dimethylformamide, N,N-dimethylacetamide or dimethylsulfoxide, or their aqueous mixtures, in the presence of a weak base such as, e.g., NaN$_3$, LiN$_3$, triethylamine, collidine and the like.

By duly considering the various processes for preparing the 4-amino-derivatives, described in GB-A-2 171 100, it appears clear that a skilled chemist can safely carry out in laboratory all the chemical reactions involved in such processes.

Indeed, even if reagents like sodium azide are used, they are only in very small amounts, namely not hazardous amounts, that can be safely handled.

However, when the above-mentioned processes are transferred from the laboratory small-scale to the industrial large-scale production, the presence of large amounts of azothydric acid and working intermediate organic azido-compounds at high temperature may involve risks.

The purpose of the present invention is therefore to provide a new process for preparing such 4-aminoderivatives, which gets round the above-considered synthesis problems and can safely be worked in the industrial large scale production.

The present invention relates to a new process for the preparation of 4-amino androstenedione derivatives having the following formula (I)

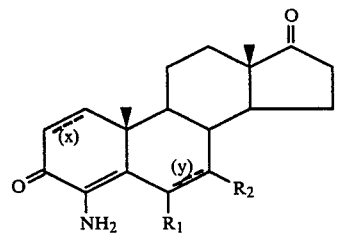

(I)

wherein
one of R$_1$ and R$_2$ is hydrogen and the other is hydrogen, C$_1$-C$_6$ alkyl, C$_2$-C$_6$ alkenyl or C$_2$-C$_6$ alkynyl; and
the symbol ≈≈≈ indicates that each of (x) and (y), independently, is a single bond or a double bond.

The invention includes also the pharmaceutically acceptable salts of the compounds of formula (I) as well as all the possible isomers of formula (I), both separately and in mixture.

In the formulae of this specification a dotted line (. . .) indicates a substituent in the α-configuration, i.e. below the plane of the ring; a wedged line (—) indicates a substituent in the β-configuration, i.e. above the plane of the ring; and a wavy line (∿) indicates that a substituent may be in the α-configuration or in the β-configuration or both. Consequently, where a formula has a substituent with a wavy line bond, the formula may represent a compound having the substituent solely in the α-configuration or solely in the β-configuration, or the formula may represent a mixture of both compounds having the substituent in the α-configuration and compounds having the substituent in the β-configuration. The alkyl, alkenyl and alkynyl groups may be branched or straight chain.

A C$_1$-C$_6$ alkyl group is, preferably, a C$_1$-C$_4$ alkyl, in particular methyl, ethyl, n-propyl or tert-butyl, more preferably methyl or ethyl.

A C$_2$-C$_6$ alkenyl group is, preferably, a C$_2$-C$_4$ alkenyl, in particular vinyl, allyl, 1-propenyl, 1-butenyl, 2-butenyl or 3-butenyl, most preferably vinyl or allyl.

A C$_2$-C$_6$ alkynyl group is, preferably, a C$_2$-C$_4$ alkynyl, in particular ethynyl, 1-propynyl, 2-propynyl, 1-butynyl, 2-butynyl or 3-butynyl.

As already said, the invention includes also the pharmaceutically acceptable salts of the compounds of formula (I). Preferred salts according to the invention are the salts of the compounds of formula (I) with pharmaceutically acceptable acids, both inorganic acids such as, e.g., hydrochloric, sulfuric or phosphoric acid, and organic acids such as, e.g., citric, fumaric, maleic, malic, ascorbic, tartaric, benzoic, acetic, phenylacetic, cyclohexylacetic, 3-cyclohexylpropionic, methanesulfonic, ethanesulfonic, benzenesulfonic, p-toluenesulfonic or p-nitrobenzenesulfonic acid.

According to the new process, which is the object of the present invention, the compounds of formula (I) and the pharmaceutically acceptable salts thereof can be prepared by a process comprising reacting a compound of formula (II)

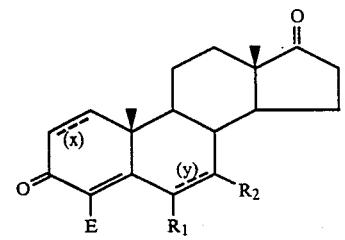

(II)

wherein
E is a halogen atom and R, R$_1$, (x) and (y) are as defined above, with ammonia and, if desired, salifying a compound of formula (I) or obtaining a free compound of formula (I) from a salt thereof.

In a compound of formula (II) E may be for example chlorine, bromine or iodine, preferably it is chlorine or bromine.

Preferably a compound of formula (II) is reached with a concentrated aqueous solution of ammonia in a solvent consisting of mixtures of water and water miscible organic solvents, such as dioxane or tetrahydrofurane, preferably mixtures of water and dioxane.

More preferably a compound of formula (II) is reacted with a mixture containing from 1.5 to 2.5 parts by volume of concentrated aqueous solution of ammonia and 1 part by volume of dioxane. Particularly preferred ratio of such mixture is 2 parts by volume of concentrated aqueous solution of ammonia to 1 part by volume of dioxane.

The reaction temperature may range from about 20° C. to about 120° C. and the reaction may take from about 4 hours to about 48 hours.

Conventional methods may be used for salifying a compound of formula (I) and for obtaining a free compound of formula (I) from a salt thereof.

The compounds of formula (II) are either known compounds or may be prepared with known methods or with methods known to the skilled in the art. For instance, a compound of formula (II) wherein E is chlorine, (x) is either a single or a double bond, (y) is a single bond, and $R_1$ and $R_2$ are as defined above may be obtained by chlorinating the respective compound of formula (III)

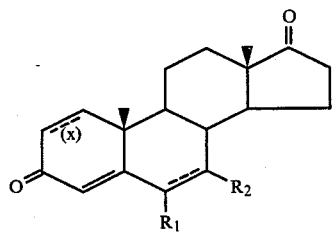

wherein $R_1$ and $R_2$ are as defined above and (x) is either a single or a double bond.

The chlorination may be carried out in a known way, for example using sulfuryl chloride and operating, e.g., in pyridine at a temperature from about 0° C. to about 60° C.

For instance, a compound of formula (II) wherein E is chlorine, (x) is either a single bond or a double bond, (y) is a double bond and $R_1$ and $R_2$ are both hydrogen, may be obtained by dehydrobromination of a compound of formula (IV)

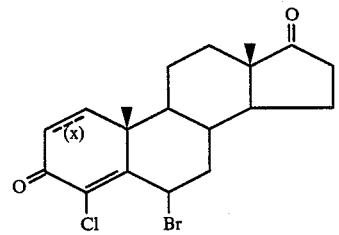

wherein (x) is either a single or a double bond. The dehydrobromination step may be carried out in a known way, for example using an organic base, preferably pyridine or collidine, and operating at a temperature from about 20° C. to about 130° C. or using an inorganic base, preferably lithium carbonate and lithium chloride in dimethylformamide, and operating at a temperature from about 60° C. to about 120° C. A compound of formula (IV) may be obtained by allylic bromination of a compound of formula (II) wherein E is chlorine, (x) is either a single or a double bond, (y) is a single bond and $R_1$ and $R_2$ are both hydrogen. The allylic bromination may be carried out with a brominating agent, e.g. N-bromosuccinimide, in an inert solvent, e.g. carbon tetrachloride, under reaction conditions well known to the skilled in the art.

For instance, a compound formula (II) wherein E is either bromine or iodine, (x) is either a single bond or a double bond, (y) is a double bond and $R_1$ and $R_2$ are both hydrogen may be obtained from a dihalo-compound of formula (V)

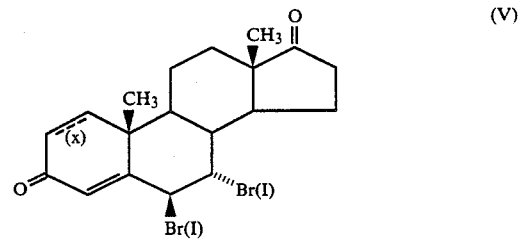

wherein (x) is either a single or a double bond, by treatment with a non nucleophilic base, e.g. pyridine, DBU or DBN, in an inert solvent, e.g. dimethylformamide, hexamethylphosphoramide, tetrahydrofurane, dioxane and operating at a temperature from about 0° C. to about 60° C. The compounds of formula (V) may be obtained by the addition of bromine or iodine to androsta-4,6-diene-3,17-dione or, respectively, to androsta-1,4,6-triene-3,17-dione according to very well known methods.

The following examples illustrate but do not limit the present invention.

EXAMPLE 1

4-aminoandrost-4-ene-3,17-dione [I, $R_1=R_2=H$, (x), (y) single bonds]

A mixture of 4-chloroandrost-4-ene-3,17-dione (1.93 g, 6 mmole), dioxane (60 ml) and 30% NH$_4$OH aqueous solution (120 ml) is stirred at room temperature during 24 hours. The organic solvent and excess of ammonia are evaporated in vacuo and the resulting aqueous residue is acidified to pH 1 by carefully adding conc. HCl. The aqueous solution is washed twice with ethyl acetate and brought to pH 11 by carefully adding conc. NaOH. The resulting precipitate is filtered off, washed with water and dried under vacuum at 40° C. There are obtained 559 mg (1.86 mmole, 31% yield) of the title compound as a white solid.

M.p. 186°–8° C.; $\nu$(cm$^{-1}$) 3430, 3350, 1740, 1660, 1590, $\lambda$(nm) 294 ($\epsilon=7354$); $\delta$0.93 (3H, s) 1.20 (3H, s) 2.90 (1H, m).

EXAMPLE 2

4-aminoandrosta-4,6-diene-3,17-dione [I, $R_1=R_2=H$, (x) single bond, (y) double bond]

A mixture of 4-bromoandrosta-4,6-diene-3,17-dione (545 mg, 1.5 mmole), dioxane (15 ml) and 30% NH$_4$OH aqueous solution (30 ml) is stirred at 75° C. in a pressure vessel during 8 hours. After cooling to room temperature, the reaction mixture is worked up as described in the Example I. There are obtained 126 mg (0.42 mmole, 28% yield) of the title compound as a yellowish solid.

M.p. 148°–50° C.; $\nu$(cm$^{-1}$) 3440, 3370, 1740, 1640, 1610, 1585, 1560; $\lambda$(nm) 347 ($\epsilon=12395$); $\delta$0.87 (3H, s) 1.00 (3H, s) 4.45 (2H, s) 6.01 (1H, dd) 6.40 (1H, dd).

By proceeding analogously, the following compounds can be prepared: 4-amino-6-methylandrosta-4,6-diene-3,17-dione; and 4-amino-7-methylandrosta-4,6-diene-3,17-dione.

EXAMPLE 3

4-aminoandrosta-1,4-diene-3,17-dione [I, $R_1=R_2=H$, (x) double bond, (y) single bond]

A mixture of 4-chloroandrosta-1,4-diene-3,17-dione (957 mg, 3 mmole), dioxane (30 ml) and 30% $NH_4OH$ aqueous solution (60 ml) is stirred at 75° C. in a pressure vessel during 18 hours. After cooling to room temperature, the reaction mixture is worked up as described in the Example 1. There are obtained 242 mg (0.81 mmole, 27% yield) of the title compound as a yellow solid.

M.p. 162°-9° C.; $\nu(cm^{-1})$ 3460, 3370, 1735, 1665, 1620, 1580; $\lambda(nm)$ 226 ($\epsilon=15509$) 322 ($\epsilon=3293$); $\delta0.94$ (3H, s) 1.23 (3H, s) 3.65 (2H, s) 6.32 (1H, d) 7.10 (1H, d).

EXAMPLE 4

4-aminoandrosta-1,4,6-triene-3,17-dione [I, $R_1=R_2=H$, (x) and (y) double bonds]

A mixture of 4-chloroandrosta-1,4,6-triene-3,17-dione (1.585 g, 5 mmole), dioxane (50 ml) and 30% $NH_4OH$ aqueous solution (100 ml) is stirred at 90° C. in a pressure vessel during 24 hours. After cooling to room temperature, the reaction mixture is worked up as described in the Example I. There are obtained 370 mg (1.24 mmole, 24% yield ) of the title compound or a yellow solid.

M.p. 206°-8° C.; $\nu(cm^{-1})$ 3460, 3380, 1730, 1645, 1620, 1560; $\delta1.00$ (3H, s); 1.19 (3H, s) 4.00 (3H, s) 5.93 (1H, dd) 6.33 (1H, d) 6.52 (1H, dd) 7.10 (1H, d).

By proceeding analogously the following compounds can be prepared: 4-amino-6-methylandrosta-1,4,6-triene-3,17-dione and 4-amino-7-methylandrosta-1,4,6-triene-3,17-dione.

EXAMPLE 5

4-aminoandrosta-4,6-diene-3,17-dione hydrochloride

A solution of 0.5 g of 4-aminoandrosta-4,6-diene-3,17-dione in 20 ml of ethanol is treated with 16.7 ml of 0.1N HCl aqueous solution. The yellow solution is then treated with 0.02 g of carbon, filtered and the alcohol is distilled at reduced pressure. The resulting aqueous solution is lyophilized to give 0.54 g of dry title compound as slightly yellow powder.

We claim:

1. A process for the preparation of a 4-aminoandrostenedione derivative of formula (I)

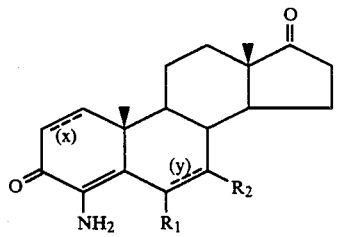

wherein one of $R_1$ and $R_2$ is hydrogen and the other is hydrogen, $C_1$-$C_6$ alkyl, $C_2$-$C_6$ alkenyl or $C_2$-$C_6$ alkynyl; and the symbol ==== indicates that each of (x) and (y), independently, is a single bond or a double bond; or a pharmaceutically acceptable salt thereof, the process comprising reacting a compound of formula (II)

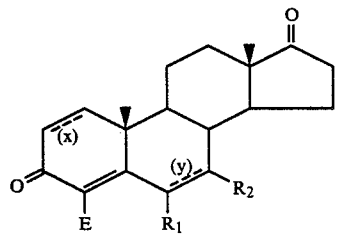

wherein E is a halogen atom and $R_1$, $R_2$, (x) and (y) are as defined above, with ammonia in an amount sufficient to obtain said derivative of formula (I) or pharmaceutically acceptable salt thereof wherein the reaction temperature may range from about 20° C. to about 120° C.

2. A process for the preparation of a 4-amino androstenedione derivative of formula (I) as defined in claim 1 or a pharmaceutically acceptable salt thereof, wherein a compound of formula (II), as defined in claim 1, is reacted with a mixture containing from 1.5 to 2.5 parts by volume of concentrated aqueous solution of ammonia and 1 part by volume of dioxane.

3. A process according to claim 2, wherein a compound of formula (II), as defined in claim 1, is reacted with a mixture containing 2 parts by volume of concentrated aqueous solution of ammonia and 1 part by volume of dioxane.

4. The process of claim 2, wherein said derivative of formula (I) is 4-aminoandrosta-4-ene-3,17-dione and said compound of formula (II) is 4-chloroandrosta-4-ene-3,17-dione.

5. The process of claim 2, wherein said derivative of formula (I) is 4-aminoandrosta-4,6-diene-3,17-dione and said compound of formula (II) is 4-bromoandrosta-4,6-diene-3,17-dione.

6. The process of claim 2, wherein said derivative of formula (I) is 4-aminoandrosta-1,4-diene-3,17-dione and said compound of formula (II) is 4-chloroandrosta-1,4-diene-3,17-dione.

7. The process of claim 2, wherein said derivative of formula (I) is 4-aminoandrosta-1,4,6-triene-3,17-dione and said compound of formula (II) is 4-chloroandrosta-1,4,6-triene-3,17-dione.

* * * * *